United States Patent [19]
Pfitzner

[11] 3,942,547
[45] Mar. 9, 1976

[54] VALVES

[76] Inventor: John Pfitzner, 87 Morton Way, London N. 14, England

[22] Filed: Aug. 13, 1974

[21] Appl. No.: 496,991

[30] Foreign Application Priority Data
Aug. 22, 1973 United Kingdom............... 39864/73

[52] U.S. Cl........... 137/102; 128/146.5; 137/512.4; 137/DIG. 9
[51] Int. Cl.²......................................... G05D 7/00
[58] Field of Search........... 128/145.8, 145.5, 145.6, 128/145.7, 146.5, 188; 137/63 R, 102, 512, 512.4; 251/61.1

[56] References Cited
UNITED STATES PATENTS

| | | | |
|---|---|---|---|
| 2,841,142 | 7/1958 | Hay.................................... | 128/188 |
| 3,419,029 | 12/1968 | Straub................................ | 137/102 |
| 3,519,012 | 7/1970 | Van Patten...................... | 137/102 |

FOREIGN PATENTS OR APPLICATIONS 1,256,024   2/1961   France............................ 128/146.5

*Primary Examiner*—William R. Cline
*Assistant Examiner*—H. Jay Spiegel
*Attorney, Agent, or Firm*—Brisebois & Kruger

[57]     ABSTRACT

A valve for directing flow of breath to and from a patient has a first port adapted to be connected to a source of breath, a second port adapted to be connected to a patient and first obturating means in the form of a diaphragm for controlling flow between the first and second ports. A passage in the valve is in continuous communication with the second port through apertures in the diaphragm and second obturating means formed by a further diaphragm controls flow from the second port through the passage. The further diaphragm is arranged to prevent flow through the passage when the first-mentioned diaphragm is allowing flow between the first and second ports.

12 Claims, 5 Drawing Figures

U.S. Patent  March 9, 1976  3,942,547
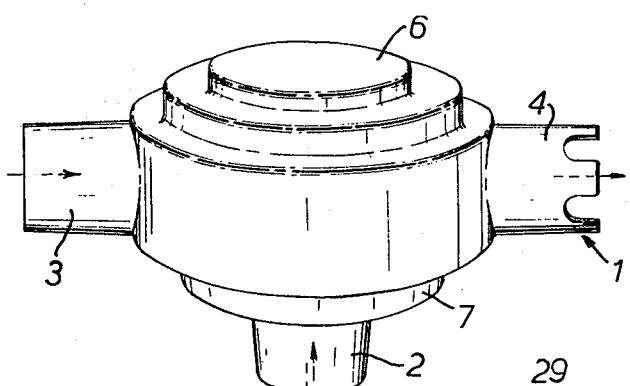
FIG./.
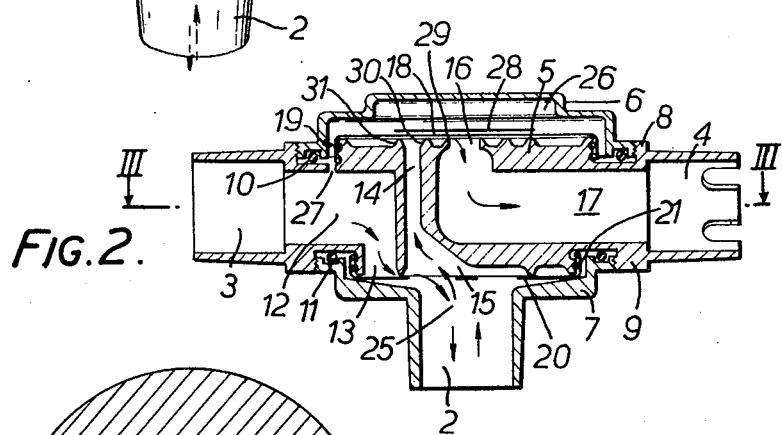
FIG.2.
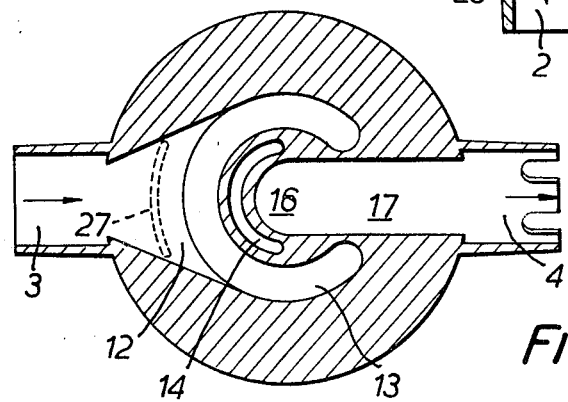
FIG.3.
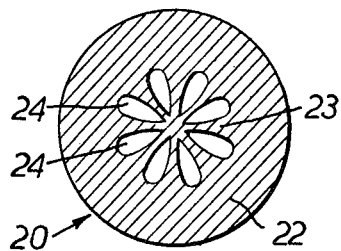
FIG.4.
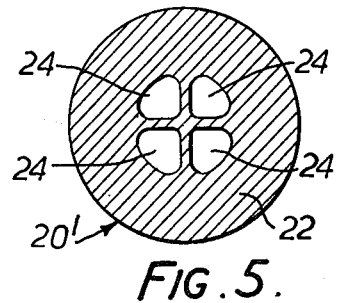
FIG.5.

VALVES

This invention relates to valves for directing the flow of breath to and from a patient.

According to the invention there is provided a valve for directing flow of breath to and from a patient, having a first port adapted to be connected to a source of breath, a second port adapted to be connected to a patient, first obturating means for controlling flow between said first and second ports, a passage in continuous communication with said second port through said first obturating means, and second obturating means for controlling flow through said passage and arranged to prevent flow through said passage when said first obturating means allows flow between said first and second ports.

In order that the invention may be well understood, an embodiment thereof, given by way of example only, will now be described reference being had to the accompanying drawings, in which:

FIG. 1 is a general perspective view of a valve in accordance with the invention;

FIG. 2 is an axial section of the same valve;

FIG. 3 is a partial view on the line III—III in FIG. 2;

FIG. 4 is a plan of a diaphragm of the valve; and

FIG. 5 is a plan of an alternative diaphragm.

Referring now to the drawings, there is shown a valve 1 for directing the flow of breath to and from a patient. The valve is provided with a port 2 for supplying the patient with breath, which for example may be a mixture of air and oxygen or anaesthetic gases, introduced into the valve 1 through an inspiration port 3, and an expiration port 4 through which expired breath from the patient passes after respiration.

Flow paths in the valve 1 are defined by passages in a substantially disc-shaped valve body 5 having side covers 6 and 7 threaded on to opposed sides 8 and 9 thereof at respective peripheral portions of the sides to form with the body 5 a valve housing. O-ring seals 10 and 11 are provided between the covers 6 and 7 and the body 5 to prevent the flow of breath between the covers and the body. In the illustrated embodiment the inspiration and expiration ports 3 and 4 are formed in the body 5 and are mutually diametrically opposed. The port 2 is formed in the cover 7.

Breath, after passing through the inspiration port 3 flows into a chamber 12 in the body 5 and thence into an annular channel 13 opening in the side 9 of the body. It will be noted that the width of the chamber 12 increases as it approaches the channel 13. A generally part annular chamber or passage 14 coaxial with the channel 13 and disposed radially inwardly thereof extends through the body 5 between the sides 8 and 9. Whilst the chamber 14 is part-annular in cross-section through most of its axial extent the portion 15 thereof at the side 9 is circular in cross-section. A tapering passageway 16 extends coaxially with and radially inwardly of the part annular portion of the chamber 14 and is connected to the expiration port 4 by a radially extending duct 17.

Obturating means in the form of a diaphragm 18 extends across the openings of the chamber 14 and passageway 16 on the side 8 of the body 5 and is secured to the body by securing means shown as a band 19 integral with the edge of the diaphragm. A rigid disc 28 is incorporated into the outer surface of the diaphragm. The diaphragm 18 controls flow between the chamber 14 and passage 16, preventing flow therebetween when in the position shown in FIG. 3 wherein the portion of the diaphragm which is made flat and rigid by the disc 28 engages with concentric circular rims 29, 30 and 31 formed as blunt knife edged projections, and allowing flow therebetween when lifted from the rims.

This arrangement results in the elimination of noisy valve-diaphragm vibration, especially at low expiratory gas flows. It should be understood that the intermediate rim 30 is not essential, the inner and outer rims 29 and 31 providing a satisfactory seat for the diaphragm, but the intermediate rim 30 increases the effectiveness of the seat.

A second obturating means in the form of a diaphragm 20 is secured to the other side 9 of the body by means shown as a band 21 to control flow from the chamber 12 to the port 2. The diaphragm 20, which is best shown in FIG. 4 has a continuous outer periphery 22 which extends across the opening of the channel 13 on the side 9 of the body and a central portion 23 provided with a plurality of circumferentially spaced apart apertures 24, which extends across the opening of the portion 15 of the chamber 14.

The diaphragm 20 in FIG. 4 has eight apertures and the alternative diaphragm 20' shown in FIG. 5 is provided with four apertures. In both diaphragms 20 and 20' the area between adjacent apertures is small such as to present no substantial resistance to flow between the port 2 and the chamber 14.

The diaphragm 20 prevents flow between the chamber 12 and port 2 when in the position shown in FIG. 2 and allows flow from the chamber 12 to the port 2 when lifted from the body. The apertures 24 in the diaphragm 20 ensure that the port 2 is in continuous flow communication with the chamber 14.

In operation, the diaphragm 20 is lifted from the body 5 when the pressure on the patient side of the diaphragm 20 is less than that in the channel 13 and breath is passed to the patient through the port 2 via a chamber 25 between the diaphragm 20 and the cover 7. When the patient expires the diaphragm 20 closes the path between the port 2 and the channel 13 and the diaphragm 18 lifts from the body 5 against pressure in a chamber 26, which is provided between the cover 6 and the diaphragm 18 and connected to the chamber 12 by channel 27, to permit expired breath to pass from the chamber 14 to the expiration port 4 through the passageway 16 and duct 17. It will be understood that the pressure in the chamber 26 prevents the diaphragm 18 from lifting when the diaphragm 20 is allowing flow from the port 3 to the port 2 and that the diaphragm 18 will lift to connect the port 2 with the port 4 when the pressure in the chamber 14 is sufficient to overcome the pressure in the chamber 26.

By tapering the passageway 16, the area of the portion of the diaphragm 18 within the inner rim 29, which is subjected to pressure through the port 4 (usually atmospheric), is reduced so that it is markedly less than the area of the remaining portion of the diaphragm 18 on the patient side thereof, and accordingly an increase in pressure in the chamber 14, which acts on the remaining portion, during expiration, readily overcomes the pressure acting on the other side of the diaphragm from chamber 26.

It will be readily appreciated that the described valve 1 can be used in the application of continuous positive airways pressure (CPAP), that is when the inspiration port is connected to a constant pressure source, and for the collection of expired breath during normal spontaneous respiration, intermittent positive pressure ventilation (IPPV), or spontaneous respiration while the patient is on CPAP, since the diaphragm 18 is arranged to close communication between the ports 4 and 2 before the diaphragm 20 lifts to allow flow between ports 3 and 2 and, thus, prevent rebreathing of expired breath through the port 4, or escape of gases from port 2 to port 4 during the inspiration phase.

A particular feature of the valve is the provision of the diaphragms 18 and 20 which when made of a suitable resilient material, for example latex, provide the valve with a low operating resistance making it suitable for use during spontaneous respiration and the construction of the valve, particularly the provision of continuous flow communication between the port 2 and the chamber 14, is such that the dead-space therein, which occurs in the chambers 14 and 25, can be minimized and this also makes the valve suitable for use during spontaneous respiration.

A safety feature of the valve is that the diaphragm 18 will lift to allow the patient to breath through the expiration port 4 should the inspiration port 3, or the supply line thereto (not shown) become blocked or kinked.

The body 5, the disc 28 and the covers 6 and 7 are preferably made of plastics material, though other material may be utilized, and advantageously the body is moulded in two halves in an acrylic material.

I claim:

1. A valve for directing flow of breath to and from a patient, having a first port adapted to be connected to a source of breath, a second port adapted to be connected to a patient, a third port adapted to convey exhaled breath from the valve, a passage between said second and third ports, a first obturating member for controlling flow between said first and second ports, said obturating member comprising a diaphragm secured at its periphery and having an intact outer portion ensuring unidirectional flow from said first port to said second port and a central apertured portion for allowing continuous communication between said second port and said passage, and a second obturating member for controlling flow between said passage and said third port and arranged to prevent flow through said passage when said first obturating member allows flow between said first and second ports.

2. A valve as claimed in claim 1, wherein the central apertured portion is provided with circumferentially spaced apart apertures.

3. A valve for directing flow of breath to and from a patient, having a first port adapted to be connected to a source of breath, a second port adapted to be connected to a patient, a third port adapted to convey exhaled breath from the valve, a passage between said second and third ports, a first obturating member for controlling flow between said first and second ports, through which obturating member said second port is in continuous communication with said passage, and a second obturating member for controlling flow between said passage and said third port and arranged to prevent flow through said passage when said first obturating member allows flow between said first and second ports, said second obturating member comprising a diaphragm, one side of which is arranged to be subjected, in use, to the pressure of flow through the first port to urge said diaphragm into a closed position to prevent flow from said passage, the pressure of which is arranged to act on a first portion of the other side of said diaphragm, a second portion of said other side being subjected to pressure through the third port.

4. A valve as claimed in claim 3, wherein said first portion is greater than said second portion.

5. A valve as claimed in claim 3, wherein said second diaphragm has a substantially rigid flat portion arranged to engage with seating means in said closed position.

6. A valve as claimed in claim 5, wherein said seating means comprise blunt knife-edged projections.

7. A valve as claimed in claim 6, wherein said first portion is annular and said second portion is disposed inwardly thereof, said projections comprising an inner rim engageable with the second diaphragm at the junction of said first and second portions and an outer rim.

8. A valve as claimed in claim 7 wherein said projections include a further rim intermediate said inner and outer rims.

9. A valve for directing flow of breath to and from a patient, having a first port adapted to be connected to a source of breath, a second port adapted to be connected to a patient, a third port adapted to convey exhaled breath from the valve, a passage between said second and third ports, a first obturating member for controlling flow between said first and and second ports, through which obturating member said second port is in continuous communication with said passage, said passage being part annular and surrounded by, though separate from, a part annular channel which connects said first port to said second port via said first obturating member, and a second obturating member for controlling flow between said passage and said third port and arranged to prevent flow through said passage when said first obturating member allows flow between said first and second ports.

10. A valve for directing flow of breath to and from a patient, having a first port adapted to be connected to a source of breath, a second port adapted to be connected to a patient, a third port adapted to convey exhaled breath from the valve, a passage between said second and third ports, a first obturating member for controlling flow between said first and second ports, through which obturating member said second port is in continuous communication with said passage, and a second obturating member for controlling flow between said passage and said third port and arranged to prevent flow through said passage when said first obturating member allows flow between said first and second ports, said second obturating member comprising a diaphragm made of thin latex rubber, with a thin flat substantially rigid disc fixed to its central portion and arranged to engage with seating means when said second obturating member is in the closed position.

11. A valve as claimed in claim 10, further including a tapering passageway located radially inwardly of said passage and in communication with said third port, and wherein said seating means comprises an inner annular blunt knife-edged projection at the opening of said tapering passageway and an outer blunt knife-edged annular projection at the opening of said passage, the edges of said projections being co-planar.

12. A valve as claimed in claim 11, wherein an intermediate blunt knife-edged annular projection is provided between said inner projection and said outer projection, the edge of said intermediate projection being co-planar with the edges of said inner and outer projections.

* * * * *